United States Patent [19]

Szilagyi

[11] Patent Number: 4,784,159

[45] Date of Patent: Nov. 15, 1988

[54] PROCESS FOR MAKING AN IMPLANTABLE DEVICE HAVING PLASMA SPRAYED METALLIC POROUS SURFACE

[75] Inventor: Paul J. Szilagyi, El Portal, Fla.

[73] Assignee: Cordis Corporation, Miami, Fla.

[21] Appl. No.: 898,007

[22] Filed: Aug. 19, 1986

[51] Int. Cl.[4] ............................................. A61N 1/04
[52] U.S. Cl. .............................. 128/784; 128/419 P; 427/34
[58] Field of Search ......................... 427/34, 122–124, 427/126.1–126.2, 248.1, 249–250, 255.1; 128/419 P, 784–786; 29/855, 874–875, 880, 885

[56] References Cited

U.S. PATENT DOCUMENTS

| | | |
|---|---|---|
| 4,011,861 | 3/1977 | Enger . |
| 4,101,984 | 7/1978 | MacGregor . |
| 4,280,514 | 7/1981 | MacGregor . |
| 4,281,669 | 8/1981 | MacGregor . |
| 4,355,426 | 10/1982 | MacGregor . |
| 4,440,178 | 4/1984 | Bussard et al. . |
| 4,542,752 | 9/1985 | DeHaan et al. . |
| 4,602,637 | 7/1986 | Elmqvist et al. ............... 128/419 P |
| 4,603,704 | 8/1986 | Mund et al. ....................... 128/784 |
| 4,606,929 | 8/1986 | Petrakov et al. ................... 427/34 |

Primary Examiner—Kyle L. Howell
Assistant Examiner—Angela D. Sykes
Attorney, Agent, or Firm—Lockwood, Alex, Fitzgibbon & Cummings

[57] ABSTRACT

An implantable device, appliance or component thereof is provided which includes a porous coating of elemental metal, which porous coating is prepared by subjecting a blend of elemental metal powder and a reductive gas atmosphere to plasma deposition conditions and spraying same onto the device, appliance or component onto which the porous coating is thereby formed.

13 Claims, 2 Drawing Sheets

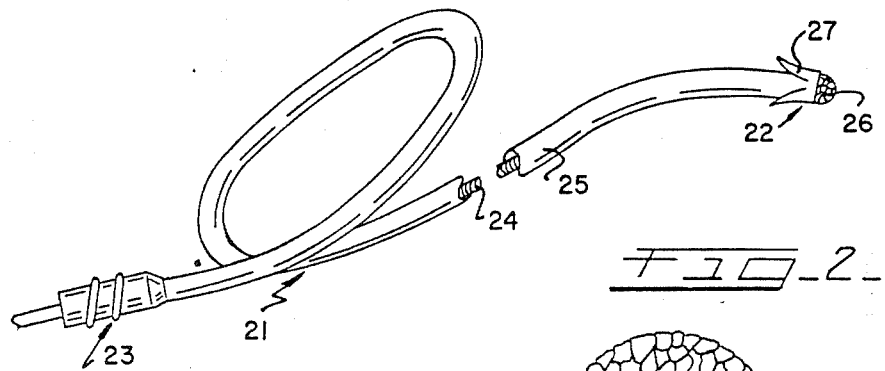
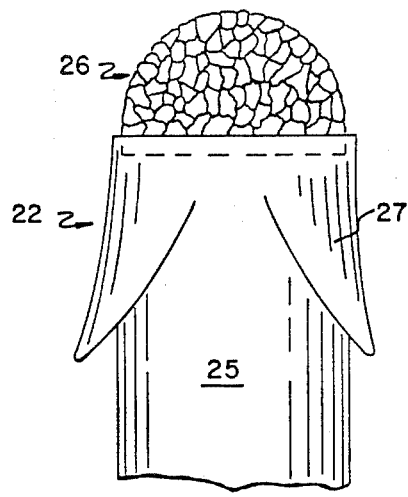
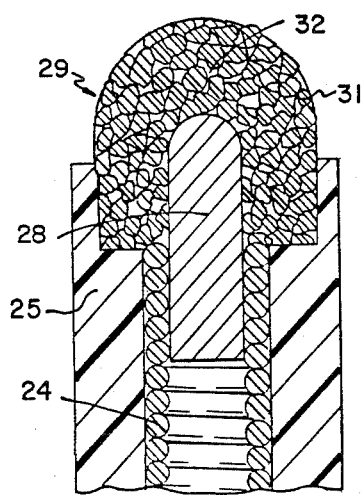
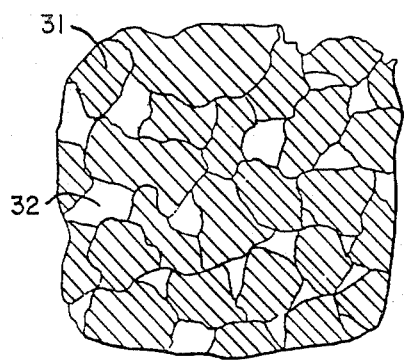

PROCESS FOR MAKING AN IMPLANTABLE DEVICE HAVING PLASMA SPRAYED METALLIC POROUS SURFACE

BACKGROUND AND DESCRIPTION OF THE INVENTION

The present invention generally relates to an implantable device or appliance having a surface which has a porous structure, the porous structure being of the type that enhances organic tissue ingrowth thereinto when the device or appliance is implanted. More particularly, the invention relates to implantable devices or appliances and to a method for producing same, such including an electrically conductive porous coating of plasma deposited elemental metal particles laid down by pressure spraying a gaseous composition onto a surface of the device, the gaseous composition including molten elemental metal powder or particles in an atmosphere of reductive gases in order to provide an environment which substantially eliminates oxidation of the metal particles in order to thereby avoid the need for subsequent treatment to remove metal oxides.

It has been recognized that in many medical applications, it is desirable to provide a tissue-compatible porous surface. The porous nature of such a surface allows tissue to grow into the porous surface in order to more effectively implant or incorporate the device or appliance into the body. Such ingrowth assists in holding the device in place within the body. Over the years, various approaches have been taken in an effort to provide tissue-compatible porous surfaces that are implantable and that promote tissue ingrowth.

Many of these prior approaches involve sintering of particles in order to form the particles into a porous network having a porosity that is suitable for promoting tissue ingrowth. Generally speaking, such sintering approaches are quite successful in providing the type of porous surface that is desired. Exemplary patents in this regard include U.S. Pat. Nos. 4,101,984 and 4,280,514. A typical sintering procedure includes forming a self-supporting coating of metallic particles which are bound to one another and to the underlying substrate by an adhesive material. Thereafter, the adhesive material or binder is dried in order to provide a preform of dried coating on the substrate, which preform is thereafter sintered to thereby bring about metal fusion of generally adjacent metal particles in order to interconnect the metal particles with one another and with the underlying metal substrate. The presintering self-supporting preform or coating of metal particles and adhesive material or binder are prepared by various procedures. For example, the metal particles may be mixed with the binder or adhesive material into a slurry which is sprayed onto the substrate or within which the substrate is dipped.

In these types of procedures, time must be taken in order to dry the substrate, binder and metal particles preform. Preform or presintering temperatures for effecting the drying require raising the materials to an elevated temperature, and the sintering procedure also requires raising the materials to an elevated temperature. Typically, presintering and sintering temperatures vary somewhat depending upon the particle size, temperature ranges in this regard being between about 2,000° F. and about 2300° F., that is between about 1,100° C. and about 1,250° C., for relatively long periods of time, usually between about 90 and 180 minutes.

Also, when it is desired to provide sintered porous surface products that are of especially superior quality, it is desirable that the metallic particles be as spherical as possible and exhibit a narrow particle size distribution. Also, the self-supporting coating must be carefully prepared prior to sintering, and it should be fixtured within the furnace, which requirements interfere with the suitability of sintering procedures for use in mass production operations.

Materials out of which these porous surface coatings have been made include porous platinum surfaces and less expensive high technology alloys, as well as carbon. Included has been the utilization of a porous carbon layer over a surface of a shaped, implantable device, appliance or implement. Typically, such porous carbon layers are laid down by sintering or other procedures that include subjecting the surfaces to high temperatures, which often results in the formation of a pyrolytic carbon coating that is vitreous or glassy and somewhat amorphous. Additionally, when carbon is laid down by a procedure such as sintering, the characteristics of sintering prevail, that is the carbon is coated in bulk quantities first, after which it is sintered under harsh treatment conditions which, for carbon, can result in a final product that is of reduced stability and uniformity.

It would accordingly be desirable to provide implantable devices which have highly electrically conductive surfaces that are of a porous nature in order to promote tissue ingrowth, which surfaces are prepared by a procedure other than sintering. Such most advantageously should lend itself to mass production by providing the porous coating without having to undergo extensive fixturing, and same should not require heating the device to high temperatures. It would also be desirable if especially superior products could be provided without having to utilize particles that are substantially spherical and/or that fall within a narrow size distribution range.

These various properties, needs and objectives are achieved by the present invention, by which a porous implantable device is provided without sintering. A supply of elemental metal powder flows with a supply of reductive gas past a power source in order to plasma deposit the elemental metal in a manner that achieves the desired porosity. The elemental metal particles are electrically conductive. After treatment in accordance with this invention, they retain their electrical conductivity without further treatment since there is no significant formation of metal oxides on the metal particles, due principally to the reductive nature of the plasma gas environment. Requiring spherical powder particles and high temperature heating of the device or implement are avoided according to the present invention, which is well suited for mass production manufacturing procedures.

It is accordingly a general object of the present invention to provide an improved implantable device including a plasma deposited porous layer.

Another object of the present invention is to provide an implantable device having a porous surface that is formed from elemental metallic particles that are pressurized and plasma deposited while avoiding oxide formation.

Another object of the present invention is to provide an improved porous-surfaced device or implement that lends itself well to being manufactured on a mass production scale.

Another object of this invention is to provide an improved implantable device or appliance that promotes colonization and tissue ingrowth into the depth of the porous surface from adjacent body tissue within which it is implanted in order to provide bonding between the body tissue host and the porous member.

Another object of this invention is to provide an implantable device having a porous surface, which device is manufactured without having to raise its temperature to a substantially high level.

Another object of the present invention is to provide an improved device and process which utilizes plasma deposition techniques for the formation of a porous implantable coating having high electrical conductivity.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is a perspective view, partially broken away, of a cardiac pacing lead having a tip electrode assembly that includes a porous member in accordance with the present invention;

FIG. 2 is an enlarged elevational view of the distal end portion and electrode of the cardiac pacing lead shown in FIG. 1;

FIG. 3 is a longitudinal cross-sectional view of the distal end portion of the lead and electrode shown in FIG. 2;

FIG. 4 is a further enlarged cross-sectional view showing details of the porous coating shown in FIG. 3;

DESCRIPTION OF THE PARTICULAR EMBODIMENTS

Figure 5:
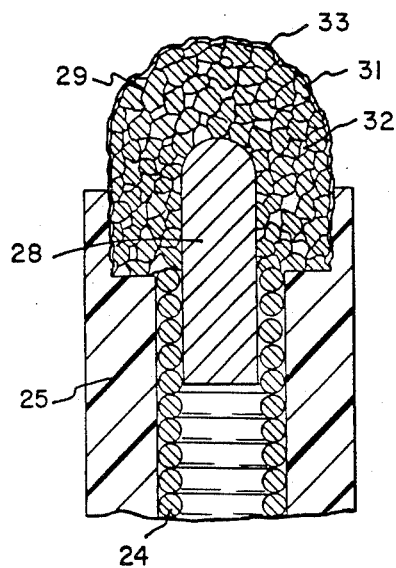
FIG. 5 is a longitudinal cross-sectional view similar to FIG. 3, but within which the porous coating is overcoated.

An illustration of the type of device within which this invention is incorporated is provided by FIG. 1. The particular device illustrated is an implantable pervenous lead, generally designated as 21, which includes a distal tip electrode assembly, generally designated as 22, and a terminal assembly, generally indicated by 23, connected together by a elongated conductor member 24 having a protective and insulative outer sheath or cover 25. The terminal assembly 23 is designed and shaped for use with an implantable cardiac pacemaker (not shown). Tip assembly 22 provides an exterior electrically conductive surface and includes an electrode 26 having a porous surface for contacting the tissue that is to be stimulated by the cardiac pacer. If desired, fins or tines 27 can be included in order to enhance the stability of the implanted distal tip electrode assembly 22.

Further details of the tip assembly are shown in FIG. 2, as well as in FIG. 3 and FIG. 5. The illustrated conductor member 24 is a tightly wound helical metal coil, and the outer sheath is a polymer such as polyurethane or the like that generally encases and is typically bonded to the conductor member 24. The electrode 26 includes a conductive shaft 28 having a porous coating 29 thereover. Porous coating 29 includes a plurality of metal particles 31 that had been formed and deposited as described herein, such metal particles 31 having areas of substantially free space or pores 32 therebetween.

Figure 6:
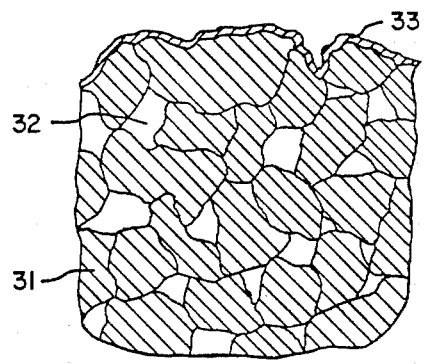
FIG. 6 is a further enlarged or magnified cross-sectional view of the porous coating and overcoating shown in FIG. 5.

In the embodiment illustrated in FIG. 5 and FIG. 6, the porous coating 29 is overlain with a conductive coating 33. Most advantageously, this conductive coating 33 is a carbon layer which may be laid down by any suitable method, such as by the use of plasma deposition techniques, through the use of a conductive epoxy, or by means of similar procedures.

Figure 7:
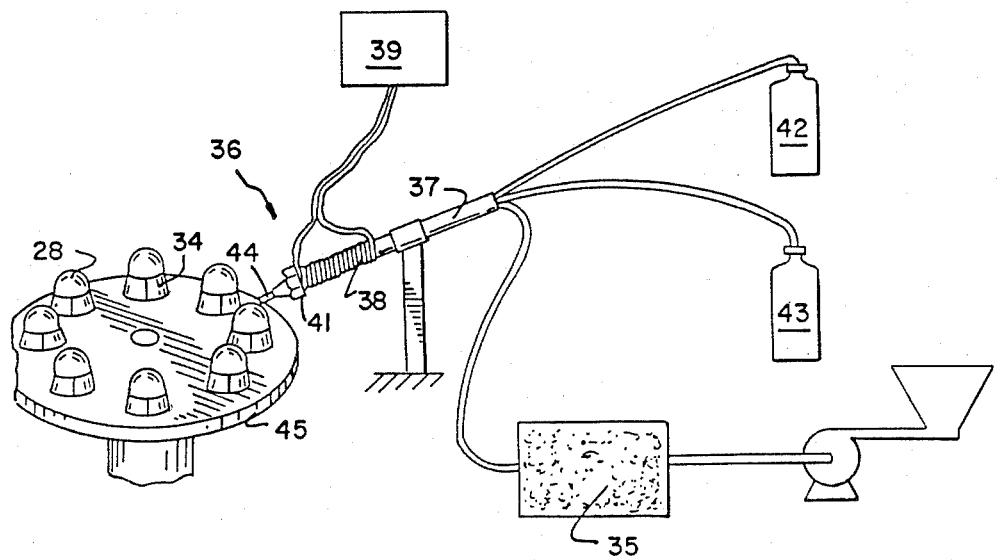
FIG. 7 is a generally schematic view of the preferred plasma deposition system suitable for laying down the porous coating of elemental particles.

Referring more particularly to the porous coating 29, such is laid down by a plasma spraying technique which can be carried out on an apparatus of the type generally illustrated in FIG. 7. The member to be rendered porous, such as the conductive shaft 28, is supported within a jig or fixture 34, which may be a component of a rotatable or otherwise movable platform 45 by virtue of which several shafts 28 or the like are mounted. The mounting may be in a manner whereby multiple shafts 28 or the like can be generally simultaneously subjected to plasma spraying in order to form the porous coating 29 thereonto. If the surface of the device being coated such as the conductive shaft 28 is too smooth, its surface can be roughened in a previous operation such as by grit blasting, exemplary grit in this regard being alumina particles.

A typical electrode shaft 28 will be made of titanium or a titanium alloy, and the metal powder of the metal particles 31 is an elemental metal such as titanium, tungsten, chromium, alloys thereof, and the like. Individual particles of this elemental metal powder need not be spherical in shape, and the powder need not exhibit a narrow particle size distribution. Generally speaking, the powder can have a particle size distribution of between about −125 to 325 mesh size (U.S. Standard Mesh Size). The resulting porous coating 29 will typically exhibit a porosity, which is the total volume of the pores 32, of between about 10 percent and about 15 percent by volume, based on the total volume of the porous coating 29.

In the illustrated arrangement, the elemental metallic powder or particles are held within a reservoir 35 which maintains the metallic powder in a pressurized condition and provides for its flow into a plasma reactor assembly 36. Plasma reactor assembly 36 includes a reactor tube or chamber 37, a conductive coil 38 wrapped therearound, and a radio frequency (or RF) power source 39 which is the source of RF power that is transmitted into the internal volume of the reactor tube or chamber 37, which power transmission is preferably carried out in conjunction with a heating arc assembly 41 at or near the distal end of the reactor tube or chamber 37. The RF power source 39 heats the plasma reactor assembly 36 and the heating arc assembly 41 provides heat energy to the extent that the temperature at the heating arc assembly 41 will be on the order of 6,000° C. (approximately 10,800° F.) and above.

In addition to the pressurized supply of metallic powder, gases also flow into and through the reactor tube or chamber 37 in order to provide the atmosphere that is plasma reacted within the reactor assembly 36. Preferably, two gas supplies 42 and 43 are included. The gas supplies mix with the metallic powder within the reactor tube or chamber 37, are subjected to RF energy and are plasma sprayed from the reactor tube or chamber 37, such as through a nozzle 44, whereby the plasma discharge is directed onto the surface onto which the porous coating of elemental metal is being deposited.

These assemblies are especially useful for mass production arrangements wherein a plurality of jigs 34 mount a plurality of conductive shafts 28 or the like, which, for example, are rotated into the area of the nozzle 44 by the operation of the platform 45 or other suitable assembly that is rotatable and/or otherwise movable in association with the plasma reactor assembly 36, which may or may not be movable, such that the plasma discharge from the plasma reactor assembly 36 will coat all desired surfaces of the conductive shafts 28 and the like. Movement of the plasma reactor assembly 36 typically will include reciprocating or back-and-forth movement so that the desired plasma deposit pattern is followed in order to lay down the desired porous coating 29. If desired, appropriate masking may be provided in order to prevent plasma deposition of the elemental metal particles onto selected locations of the conductive shaft 28 or the like onto which the porous metallic coating is not to be deposited. By platform rotation or other movement, the sides of the conductive shafts 28 or the like are coated. Several hundred conductive shafts 28 or the like can be imparted with a porous coating according to this invention during a single operation without requiring extensive fixturing.

When the pressurized supply of elemental metallic powder is forced into the reactor tube or chamber 37 within the reductive gas atmosphere provided from the gas supplies 42 and 43, the plasma reactor assembly 36 causes the elemental metallic particles to become molten, and these molten metallic droplets are sprayed onto each conductive shaft 28 or the like. Because the conductive shaft 28 or the like is at approximately room temperature, the molten droplets solidify or "freeze", during which solidification procedure they are fused onto the surface of each conductive shaft 28 or the like. Such molten droplets likewise also fuse generally together to form the porous coating 29 having the pores 32. It will be observed that, because the elemental metal particles are melted, the shape of the metal powder within the reservoir 35 is not particularly critical since the particles are melted and are thereby modified from their original configuration.

By this procedure, each conductive shaft 28 or the like will be raised to a relatively low temperature temperature of on the order of about 300° C. (approximately 570° F.), such heating being due to the absorption of heat from the molten metal droplets. This temperature is significantly lower than temperatures to which substrates and coatings must be subjected in previously practiced sintering procedures. The thickness of the porous coating 29 will typically range from between about 20 and 300 microns, but can be as thick as up to about 500 microns.

Because the gases provided by the gas supplies 42, 43 provide a reductive atmosphere, there is no significant oxidation of the elemental metal of the metal powder and of the metal droplets that form the porous coating 29. Because of this, no subsequent treatment such as fluoride etching is needed in order to remove metal oxides of the porous coating 29. Preferably, the reductive atmosphere includes a generally inert gas in combination with a gas having superior reductive properties. The preferred gas having reductive properties is hydrogen gas, and inert gases include argon, helium and neon.

The preferred reductive atmosphere is provided by a supply of argon and a supply of hydrogen.

When the illustrated pervenous lead 21 is prepared, the resulting porous coated conductive shaft 28 is spot welded at a non-administration surface thereof to the conductor member 24, after which the protective and insulative outer sheath or cover 25 is applied as needed in order to cover all or substantially all of the outer surface of the conductor member 24. When desired, the fins or tines 27 or the like are bonded onto or otherwise formed on the protective and insulative outer sheath of cover 25.

The illustrative embodiment of a porous device or element according to this invention takes the form of a conductive shaft for forming a tip electrode of a pervenous lead. However, the invention is suitable for preparing various other implantable devices or components thereof having a metallic porous surface. Examples include blood engaging element of heart valves, blood pumps, and the like.

When desired, and depending somewhat upon the particular porous device or component that is being manufactured, the elemental metal porous coating 29 can be overlaid by the conductive carbon coating 33 shown in FIG. 5 and in FIG. 6. Such a carbon coating 33 is applied by an appropriate method, such as by plasma deposition, by conductive epoxy procedures, or by similar methods.

Although plasma deposition techniques are generally known, it is to be understood that when the term plasma is used herein, such refers to a state that a gas achieves when it is excited to the point of ionization, which is the region in which an active species of the gas is actually formed. The excitation is achieved in the present instance by the energy from from the RF power source 39 which is conveyed to the gaseous environment within the plasma reactor assembly 36.

It will be understood that the embodiments of the present invention which have been described are illustrative of some of the applications of the principles of the present invention. Numerous modifications may be made by those skilled in the art without departing from the true spirit and scope of the invention.

I claim:

1. A device or appliance that is implantable in organic tissue and that has a surface for enhancing organic tissue ingrowth thereinto, the device or appliance having been made by a process comprising:
    providing a shaped substrate member having an electrically conductive surface;
    blending a supply of electrically conductive elemental metal particles with a reductive gaseous environment in order to form a plasma deposition blend, said reductive gaseous environment including a reductive gas that substantially eliminates oxidation of the elemental metal particles during their subsequent plasma deposition within said reductive gaseous environment;
    subjecting said plasma deposition blend to a source of energy in order to plasma excite said plasma deposition blend within said reductive gaseous environment;
    spraying said excited plasma deposition blend onto said electrically conductive surface of the shaped substrate member within said reductive gaseous environment in order to thereby form a porous coating of substantially unoxidized elemental metal and pores onto said electrically conductive surface of the shaped substrate member; and said steps of subjecting said plasma deposition blend to a source of energy in order to plasma excite it and spraying said excited plasma deposition blend onto said electrically conductive surface raise the temperature of the electrically conductive surface to a temperature significantly lower than a metal sintering temperature.

2. The implantable device or appliance according to claim 1, wherein said subjecting step heats said elemental metal particles to a substantially molten state, and said spraying step directs said substantially molten elemental metal particles onto said electrically conductive surface, after which said substantially molten elemental particles solidify into said porous coating.

3. The implantable device or appliance according to claim 1, further including applying a conductive coating over said porous coating.

4. The implantable device or appliance according to claim 1, further including applying a conductive carbon coating over said porous coating.

5. The implantable device or appliance according to claim 1, wherein said elemental metal particles are selected from the group consisting of titanium, tungsten, chromium and alloys thereof.

6. The implantable device or appliance according to claim 1, wherein said reductive gas is hydrogen gas.

7. The implantable device or appliance according to claim 1, wherein said reductive gaseous environment further includes an inert gas.

8. A process for making a porous component of a device or appliance that is implantable in organic tissue, the porous component having a surface for enhancing organic tissue ingrowth thereinto, comprising:

providing a shaped substrate member having an electrically conductive surface;

blending a supply of electrically conductive elemental metal particles with a reductive gaseous environment in order to form a plasma deposition blend, said reductive gaseous environment including a reductive gas that substantially eliminates oxidation of the elemental metal particles during their subsequent plasma deposition within said reductive gaseous environment;

subjecting said plasma deposition blend to a source of energy in order to plasma excite said plasma deposition blend within said reductive gaseous environment;

spraying said excited plasma deposition blend onto said electrically conductive surface of the shaped substrate member within said reductive gaseous environment in order to thereby form a porous coating of substantially unoxidized elemental metal and pores onto said electrically conductive surface of the shaped substrate member; and said steps of subjecting said plasma deposition blend to a source of energy in order to plasma excite it and spraying said excited plasma deposition blend onto said electrically conductive surface raise the temperature of the electrically conductive surface to a temperature significantly lower than a metal sintering temperature.

9. The process according to claim 8, wherein said subjecting step heats said elemental metal particles to a substantially molten state, and said spraying step directs said substantially molten elemental metal particles onto said electrically conductive surface, after which said substantially molten elemental particles solidify into said porous coating.

10. The process according to claim 8, further including applying a conductive coating over said porous coating.

11. The process according to claim 8, wherein said elemental metal particles are selected from the group consisting of titanium, tungsten, chromium and alloys thereof.

12. The process according to claim 8 wherein said reductive gaseous environment includes an inert gas.

13. The process according to claim 8, wherein said subjecting and spraying steps raise the electrically conductive surface to a temperature on the order of approximately 300° C.

* * * * *